(12) United States Patent
Siccardi et al.

(10) Patent No.: US 11,058,438 B2
(45) Date of Patent: Jul. 13, 2021

(54) GUIDE FOR INTRAMEDULLARY REAMER

(71) Applicant: MEDACTA INTERNATIONAL S.A., Castel San Pietro (CH)

(72) Inventors: Francesco Siccardi, Castel San Pietro (CH); Massimiliano Bernardoni, Castel San Pietro (CH); Frederic Laude, Castel San Pietro (CH); Andrea Terruzzi, Castel San Pietro (CH)

(73) Assignee: MEDACTA INTERNATIONAL S.A., Castel San Pietro (CH)

( * ) Notice: Subject to any disclaimer, the term of this patent is extended or adjusted under 35 U.S.C. 154(b) by 158 days.

(21) Appl. No.: 16/462,128

(22) PCT Filed: Nov. 16, 2017

(86) PCT No.: PCT/IB2017/057165
§ 371 (c)(1),
(2) Date: May 17, 2019

(87) PCT Pub. No.: WO2018/092055
PCT Pub. Date: May 24, 2018

(65) Prior Publication Data
US 2019/0328401 A1 Oct. 31, 2019

(30) Foreign Application Priority Data
Nov. 17, 2016 (IT) .................. 102016000116509

(51) Int. Cl.
*A61B 17/16* (2006.01)
*A61B 17/17* (2006.01)

(52) U.S. Cl.
CPC ........ *A61B 17/164* (2013.01); *A61B 17/1631* (2013.01); *A61B 17/1633* (2013.01);
(Continued)

(58) Field of Classification Search
CPC . A61B 7/164; A61B 17/1633; A61B 17/1631; A61B 17/1717; A61B 17/1721; A61B 17/1725
See application file for complete search history.

(56) References Cited

U.S. PATENT DOCUMENTS 6,083,225 A 7/2000 Winslow et al.
2003/0220646 A1 11/2003 Thelen et al.
(Continued)

FOREIGN PATENT DOCUMENTS

EP 1132051 A2 9/2001
JP H10-200 A 1/1998
(Continued)

OTHER PUBLICATIONS

International Search Report for PCT/IB2017/057165, dated Feb. 19, 2018, 3 pages.
(Continued)

*Primary Examiner* — Matthew J Lawson
(74) *Attorney, Agent, or Firm* — Meunier Carlin & Curfman LLC

(57) ABSTRACT

Various implementations include a guide for intramedullary reamer; that includes a central body adapted to be received in a medullary canal and defining an inlet opening and an outlet opening, communicating with each other by an axial cavity, passing inside the central body, adapted to receive a reamer inside it. The central body defines at least one non-rectilinear portion, interposed between the inlet opening and the outlet opening, shaped so as to guide the reamer inside the medullary canal, in axial alignment. The non-rectilinear portion defines a window adapted to facilitate the insertion of the reamer inside said central body.

17 Claims, 5 Drawing Sheets

(52) U.S. Cl.
CPC ...... *A61B 17/1717* (2013.01); *A61B 17/1668* (2013.01); *A61B 17/175* (2013.01)

(56) References Cited

U.S. PATENT DOCUMENTS

| | | | |
|---|---|---|---|
| 2012/0109130 A1* | 5/2012 | Casey | A61B 17/1631 606/79 |
| 2012/0150301 A1* | 6/2012 | Gamache | A61F 2/4455 623/17.16 |
| 2014/0207142 A1* | 7/2014 | Takeuchi | A61B 17/1617 606/80 |
| 2017/0007272 A1* | 1/2017 | Weitzman | A61B 17/1631 |
| 2017/0100136 A1* | 4/2017 | Dougherty | A61B 17/1633 |

FOREIGN PATENT DOCUMENTS

| | | |
|---|---|---|
| JP | 2001293017 A | 10/2001 |
| JP | 2003522585 A | 7/2003 |
| JP | 2014128313 A | 7/2014 |
| JP | 2015134204 A | 7/2015 |
| WO | WO9952453 A2 | 10/1999 |
| WO | 0160262 A1 | 8/2001 |

OTHER PUBLICATIONS

Notice of Reasons for Refusal issued in JP 2019-526309, dated May 27, 2020, 8 pages.

* cited by examiner

GUIDE FOR INTRAMEDULLARY REAMER

The present application is a National Phase Entry of PCT International Application No. PCT/IB2017/057165, which was filed on Nov. 16, 2017, and which claims priority to application Ser. No. 10/201,6000116509 filed in Italy on Nov. 17, 2016, the contents of which are hereby incorporated by reference.

The present invention relates to a guide for intramedullary reamer. Generally, in arthroplasty operations, for example in hip arthroplasty operations, particularly when preparing the femoral canal, the need is highlighted to use reamers, commonly known by the English name of reamers, which are studied and designed specifically for being inserted into the medullary canal of a bone, for example the femur.

During joint replacement operations, it is common practice to remove bone parts and replace them with prostheses made of various biocompatible material, such as, for example titanium alloys, ceramic and similar. In order to secure such parts of the prosthesis to the human body, said prostheses must be joined to the patient's bone structure by various techniques. One of these techniques includes accessing the medullary canal of one or more bones to insert a portion of the prosthetic apparatus. By way of example, taking a hip joint replacement operation carried out by means of an anterior approach using a minimally invasive technique, it is known that a portion of the prosthesis, said stem, is inserted into the medullary canal of the femur. In order to proceed with the insertion, the surgeon must prepare the medullary canal by creating the space inside to receive the stem. Therefore, it will be necessary to remove part of the bone tissue to enlarge the medullary canal. This procedure is carried out by a surgeon using special rasps and reamers. Said instrument presents two possible configurations: with a flexible handle or a rigid handle. A reamer with a flexible handle is usually used for this type of operation as the flexible handle facilitates its insertion into the femoral medullary canal preventing contact with the soft tissue around the bone and consequently possible damage.

It is therefore clear how it is necessary to make the reamer perform a curved trajectory in order to align it with the axis of the medullary canal thus proceeding with its insertion inside said canal.

Using the reamer with a flexible handle, which is known in the state-of-the-art, the surgeon proceeds in a rectilinear direction through the area of the head of the femur until he/she is in correspondence with the axis of the medullary canal. At this point, the surgeon must bend the flexible handle of the reamer to align the material removal tip with the axis of the medullary canal and then proceed with creating the seat for housing the stem. The empirical nature of this curvature of the flexible handle puts surgeons in difficulty; based on their experience, the limited visibility they may have of the operative site and their skill, they judge how much the flexible handle of the reamer must bend in order to achieve the alignment with the axis of said canal.

Not only, during operations of bone removal to create the seat of the stem, the curvature imposed on the handle may cause the tip of the reamer to rasp on a wall of the medullary canal, thus removing bone material in an eccentric manner. This type of imperfect removal weakens the bone structure around the area where the stem is to be positioned, with consequent possible bone fractures.

Furthermore, this type of operation requires great manual skill, considerable concentration and is time-consuming for surgeons as they are obliged to proceed extremely slowly, constantly checking the alignment of the head of the reamer with the axis of the medullary canal. Moreover, it is particularly difficult to see an incorrect alignment between the head of the reamer and the axis of the canal into which it is inserted because in this type of minimally invasive operation, the operative site has reduced dimensions and is often obstructed by bodily fluids. An expert in the field can easily imagine how the consequences of an incorrect alignment can result in damage to the patient's bone structure, also serious damage, even compromising the successful outcome of the arthroplasty operation.

In order to overcome the drawbacks of what is known in the state-of-the-art, the present invention comprises a guide for intramedullary reamer, which allows the surgeon to access the medullary canal of the patient's bone through a trajectory imposed by the guide. By way of example, taking into consideration the case of a hip joint replacement operation, the surgeon can thus proceed with inserting the reamer into the medullary canal without having to act on the flexible handle of the reamer in any way to align its head with the axis of the medullary canal. Furthermore, due to its opportune characteristic dimensions and shape, the self-centering of the guide for intramedullary reamer allows the surgeon not to have to check the positioning of the head of the reamer and to proceed without hesitation with the removal of the bone necessary for creating the housing into which the stem is to be inserted.

The correct trajectory to be given to the movement of the reamer entering the medullary canal is given to the instrument by the guide for intramedullary reamer thanks to its characteristic curvature.

Other characteristic dimensions of the body of the guide for intramedullary reamer, such as, for example the thickness of the walls, the curvature radius, the outer curvature angle, the axial development and its external diameter guarantee correct self-centering without any intervention by the surgeon to correct the positioning.

In this way, the surgeon is relieved of tasks, which are often difficult to carry out correctly, avoiding potential human error related to incorrect positioning.

Thus, the object of the present invention is to facilitate and speed up the surgeon's work, besides improving the patient's safety, by eliminating potential causes of damage to the bone structure.

Said objects are achieved by a guide for intramedullary reamer having the characteristics of one or more of the appended claims.

These and other characteristics, as well as the relative technical advantages will become clearer from the following description, given by way of example and therefore not limiting, of a preferred embodiment, which is thus non-exclusive, of a guide for intramedullary reamer as illustrated in the appended figures, wherein.

Figure 1:
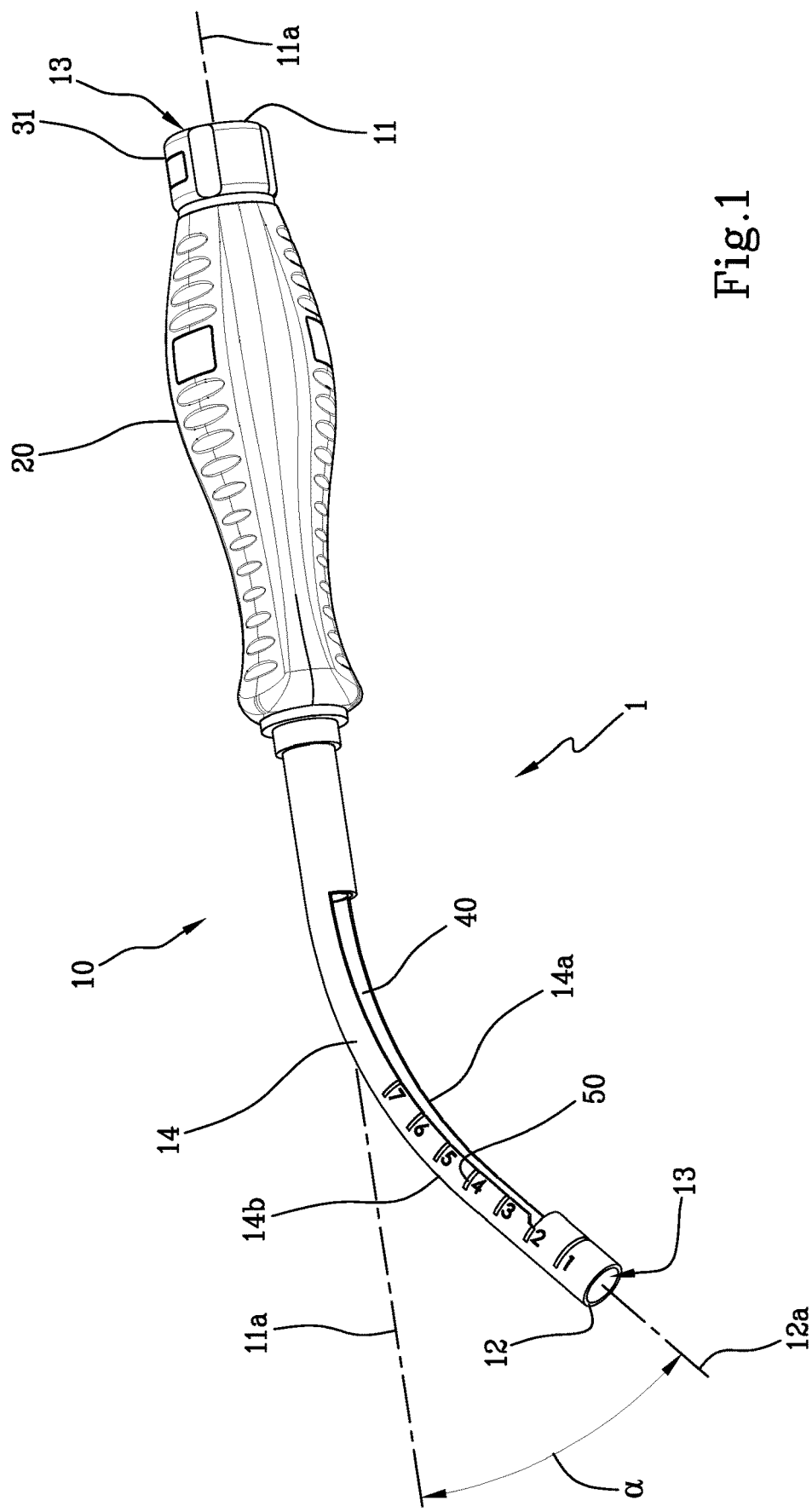
FIG. 1 is a perspective view of a first embodiment of a guide for intramedullary reamer according to the present invention.

In the following description, the term proximal is understood to mean the part of the guide for intramedullary reamer closest to the patient when said guide is installed. Similarly, the term distal indicates the part of the guide for intramedullary reamer furthest in relation to the patient's body when said guide is installed.

With reference to the drawing, 1 indicates the guide for intramedullary reamers according to a first embodiment.

Figure 3:
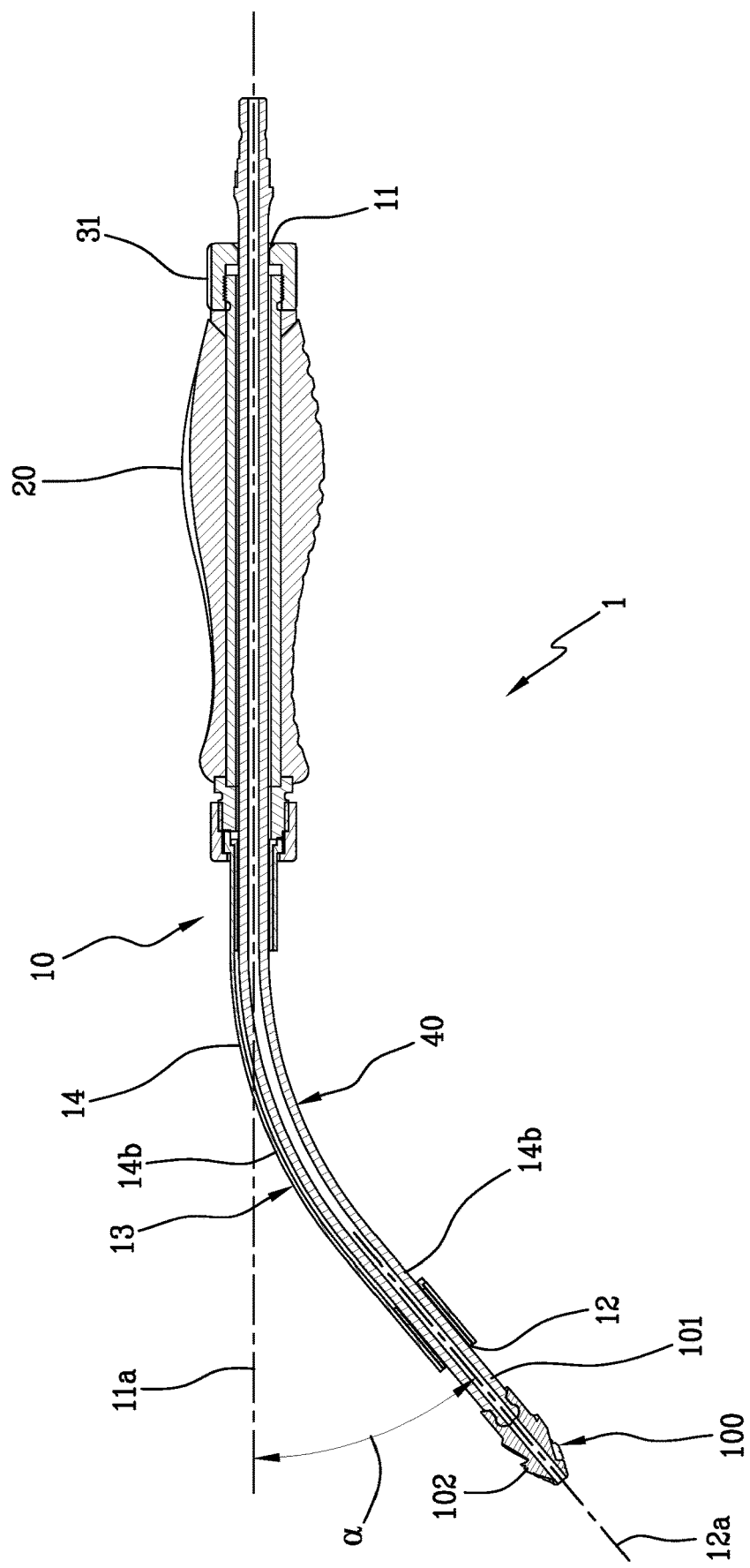
FIG. 3 is a section view of the guide for intramedullary reamer according to the embodiment illustrated in FIG. 2.

Such guide serves to guide a reamer 100 (visible in FIG. 3), which can be electric or manual, into the medullary canal.

It presents a central body 10 adapted to be received, at least partially, in a medullary canal of the patient's bone and presents an inlet opening 11 and an outlet opening 12, communicating with each other by a passing axial cavity 13, adapted to receive the reamer 100 inside it. Said central body 10 presents at least one non-rectilinear portion 14 shaped, at least partially, in an arch, so as to guide the flexible reamer into the medullary canal of the patient's bone, in axial alignment, when installed.

Figure 2:
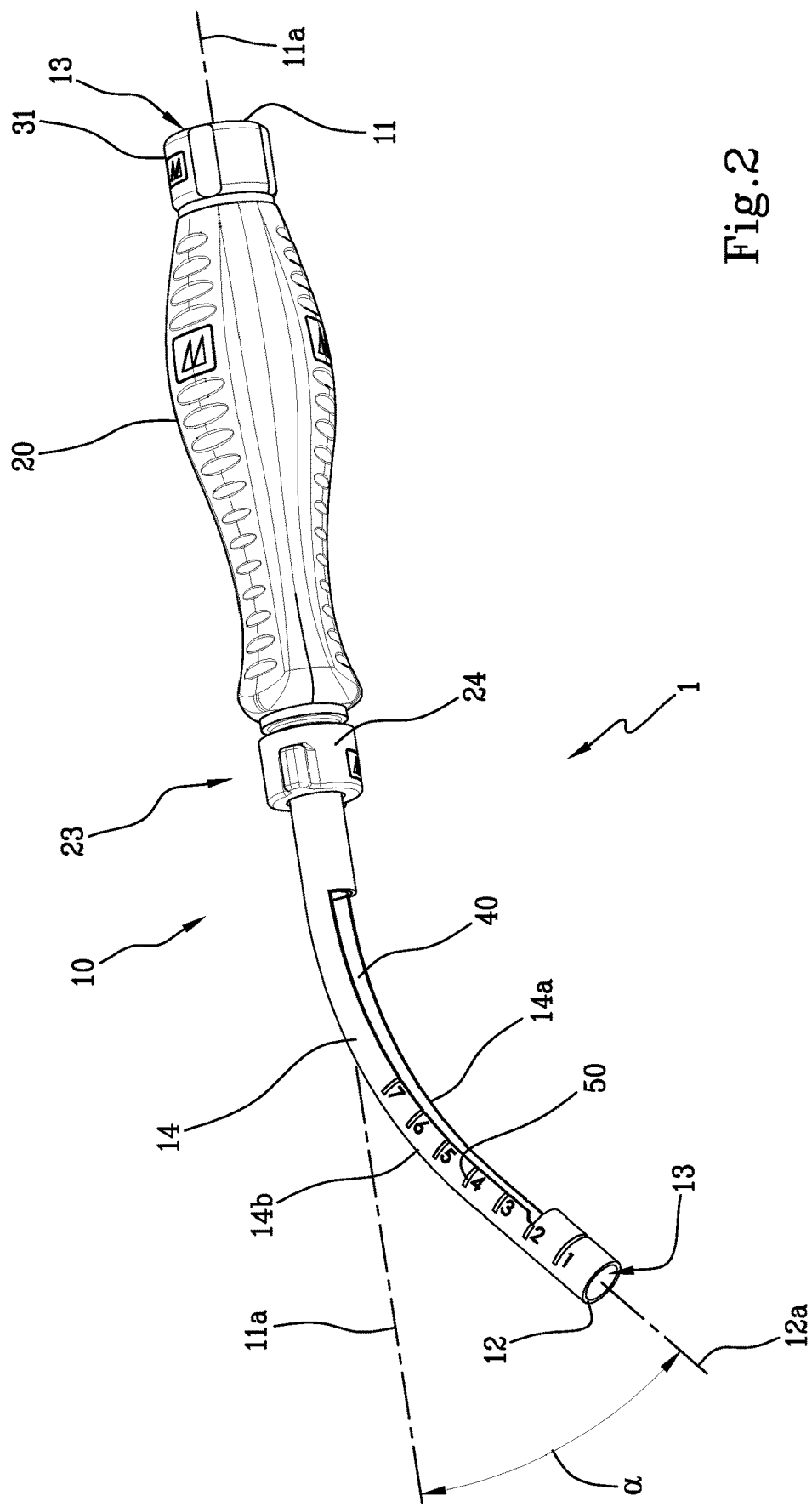
FIG. 2 is a perspective view of a second embodiment of the guide for intramedullary reamer according to the present invention.

As illustrated in FIGS. 1 and 2, the non-rectilinear portion 14 presents a window 40 adapted to facilitate the insertion of the reamer 100 inside the central body 10.

Specifically, the non-rectilinear portion 14 is arcuate and therefore has a concave part 14a and a convex part 14b. The window 40 is preferably made on the concave part 14a. In this way, the reamer 100, inserted inside the central body 10 is not obliged to conform to the curvature of the central body 10 along the whole of its path, but it is only deviated in the last section of the non-rectilinear portion 14. This prevents possible damage to the reamer 100 and to the guide itself.

In FIGS. 1 and 2 the window 40 extends partially along the axial extension of the central body 10.

Figure 4:
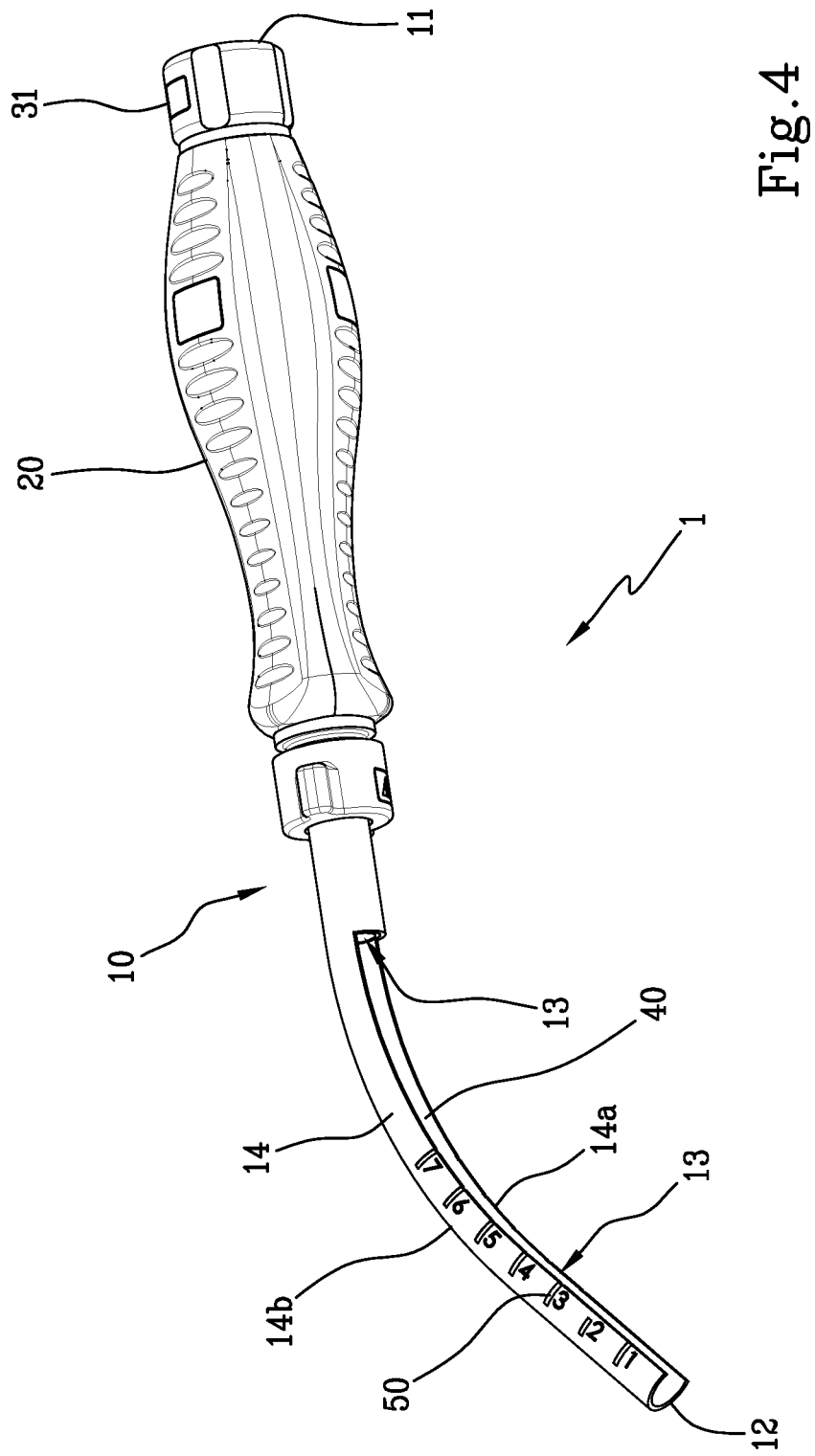
FIG. 4 is a perspective view of a third embodiment of the present invention.
Figure 5:
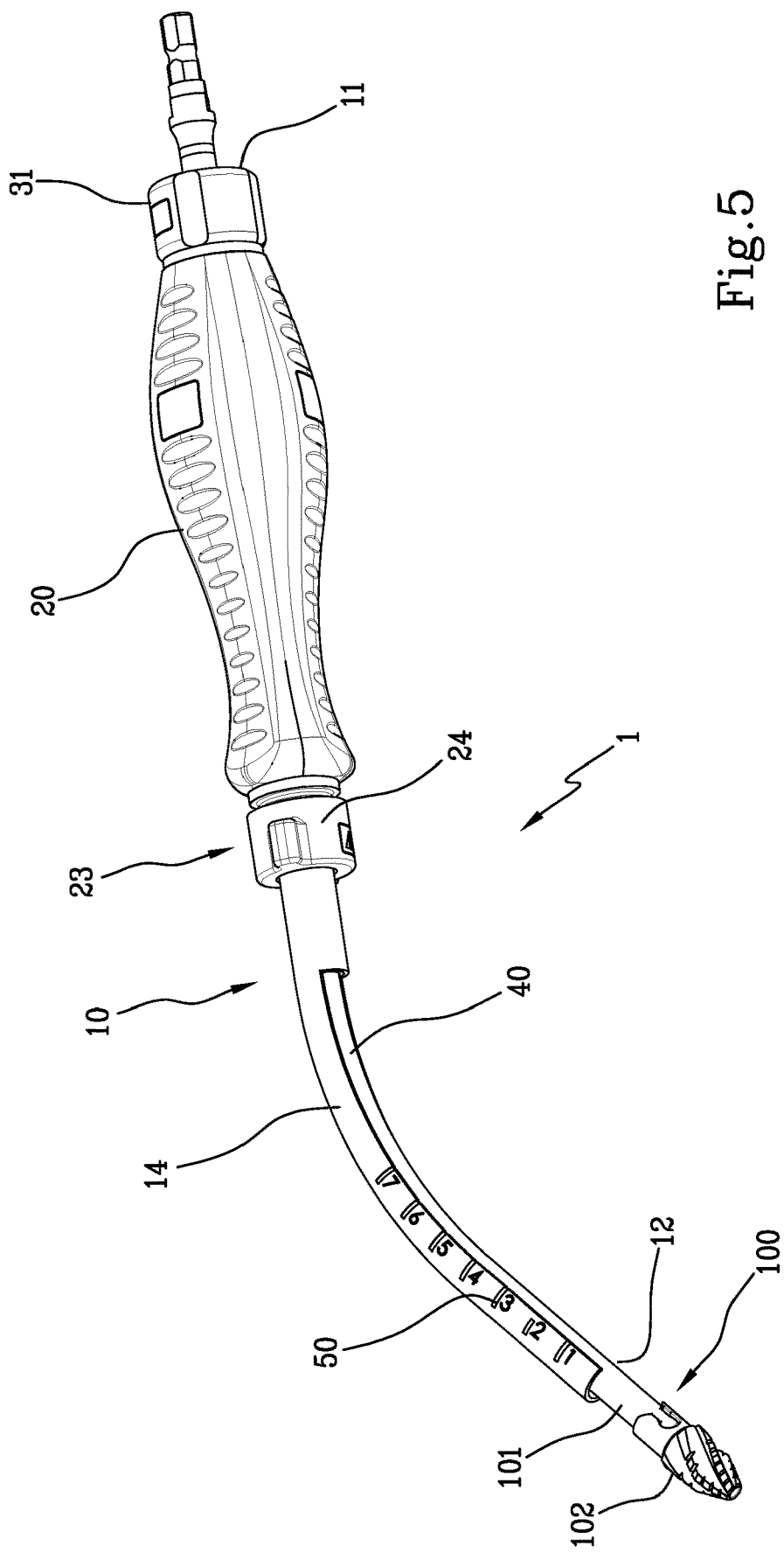
FIG. 5 is a perspective view of the third embodiment illustrated in FIG. 4, with the reamer appended.

In a variation of the first embodiment illustrated in FIG. 4, the central body 10 presents a "U" cross-section, determining an open sky axial cavity 13 adapted to receive the reamer 100 inside it. In other words, the non-rectilinear portion 14 has a window 40, which extends along the whole axial extension of the central body 10.

The non-rectilinear portion 14 also presents a graduated scale 50 positioned on the outer surface of the central body 10 adapted to indicate the insertion depth of the reamer 100 inside the medullary canal.

When installed, the central body 10 sees its end 12 inserted inside said medullary canal.

The central body 10 also comprises a handle 20 in proximity to the inlet opening 11.

The handle 20 is preferably made in the shape of a grip with a loop grasp portion.

In a first embodiment illustrated in FIG. 1, the non-rectilinear portion 14 is integrally formed with the handle 20.

Whereas, a second embodiment includes the non-rectilinear portion 14 connectable to the handle 20 by interconnection means 23, for example threaded coupling, bayonet or interlocking.

In the present embodiment, the interconnection means 23 present a bushing 24.

The interconnection means 23 are hollow internally to maintain the fluid communication between the non-rectilinear portion 14 and the handle 20. In correspondence with the inlet opening 11, the guide for intramedullary reamer 1 presents a terminal bushing 31 integrally formed with the opening 11 or coupled thereto by threaded coupling or similar.

The bushing 31 is a protective element for the moving parts of the reamer situated downstream of the flexible handle 101 of the reamer.

Advantageously, the bushing 31 is made of anti-friction material, for example Teflon. Additional anti-friction bushing can be inserted into the non-rectilinear portion 14.

The anti-friction material composing the bushing 31 guarantees that undue interaction between the guide for intramedullary reamer 1 and the moving parts of the reamer do not damage the latter.

Installation.

The following description, given by way of example, illustrates the installation of the present invention with reference to an operating technique of minimally invasive hip replacement surgery. However, it is clear to an expert in the field how said installation can easily be adapted to surgery carried out on any bone in the human body.

After creating an access to the medullary canal of the patient's bone, for example by creating an access through the greater trochanter or the head of the femur towards the femoral medullary canal, the surgeon inserts the outlet opening 12 of the central body 10 into the femoral medullary canal. In this way, at least the proximal part of the central body 10 is inside the femur.

The reamer 100, which runs inside the axial cavity 13 until it comes out of the opening 12, is inserted through the inlet opening 11 and its relative bushing 31. The reamer 100 chosen for this type of operation comprises a flexible handle portion 101 bearing a bore head 102 on its free end. During the insertion of the reamer 100 into the axial cavity 13, the flexible handle 101 adapts its shape to the curvature imposed by the central body 10 and, in particular, by the non-rectilinear portion 14. In this way, when the bore head 102 comes out of the outlet opening 12 it is automatically aligned with the axis of the intramedullary canal and self-centered in relation to it. After positioning the reamer, the steps of boring the medullary canal are completed and, at the end of this operation, the reamer and the bore guide 1 are removed.

The advantageous alignment of the bore head 102 with the medullary canal is guaranteed by the shape of the guide described above, as well as by the characteristic dimensions of said guide.

In fact, the guide for intramedullary reamer 1, the subject of the present invention, presents the non-rectilinear portion 14 preferably with an arcuate shape.

Advantageously, the central axis 12a passing through the outlet opening 12 and the central axis 11a passing through the inlet opening 11 form between them an angle α comprised between 10° and 130°, preferably between 20° and 100°. The central body 10 of the guide for intramedullary reamer 1 presents an axial extension comprised between 25 mm and 400 mm, preferably between 50 mm and 350 mm. Furthermore, the curvature radius R of the non-rectilinear portion 14 of the central body 10 is comprised between 25 mm and 400 mm, preferably between 50 mm to 300 mm.

By choosing the appropriate parameters from those indicated above, it will be possible to achieve a guide for intramedullary reamer, which can center itself in relation to the medullary canal of the bone subjected to the surgical treatment, besides relieving the surgeon of the task of acting on the flexible handle of the reamer to align it with the axis of the medullary canal.

In fact, this task will be carried out by the non-rectilinear portion 14 of the guide for intramedullary reamer 1, also preventing undue interaction between the bore head of the reamer and the walls of the medullary canal. The creation of the space needed to house the stem inside the medullary canal ends when the flexible handle of the reamer is completely inserted inside the axial cavity 13. In this configuration, the movement generating parts of the reamer arranged in the distal area of the flexible handle of the reamer may come into contact with the bushing 31. The guide for intramedullary reamer can be made of plastic material. However, said guide may also be made of metal material.

It is clear to an expert in the field how the present invention prevents the occurrence of inopportune errors of alignment of the reamer inside the medullary canal, thus avoiding eccentricity of the reamed area, damage to the patient's bone structure, undue removal of material and localized weakening of the patient's skeletal system, guaranteeing quick and easy use for surgeons, also in the case of minimally invasive operations.

The invention claimed is:

1. A guide for intramedullary reamer, comprising:
   a central body adapted to be received in a medullary canal and defining an inlet opening and an outlet opening, communicating with each other by an axial cavity, passing inside the central body, adapted to receive a reamer inside the central body;
   said central body comprising at least one non-rectilinear portion, interposed between the inlet opening and the outlet opening, shaped so as to guide the reamer inside the medullary canal, in axial alignment, wherein said non-rectilinear portion defines a window adapted to facilitate the insertion of the reamer inside said central body.

2. The guide for intramedullary reamer according to claim 1, wherein the non-rectilinear portion comprises at least a partially arcuate shape, with a concave part and a convex part.

3. The guide for intramedullary reamer according to claim 2, wherein said window is defined on the concave part of said non-rectilinear portion.

4. The guide for intramedullary reamer according to claim 3, wherein said non-rectilinear portion comprises a graduated scale for indicating the insertion depth of the reamer inside the medullary canal.

5. The guide for intramedullary reamer according to claim 1, wherein a central axis passing through the outlet opening and a central axis passing through the inlet opening form between them an angle comprised between 10° and 130°.

6. The guide for intramedullary reamer according to claim 5, wherein the angle is between 20° and 100°.

7. The guide for intramedullary reamer according to claim 1, wherein the central body presents an axial extension comprised between 25 mm and 400 mm.

8. The guide for intramedullary reamer according to claim 1, wherein an outer diameter of the central body is comprised between 3 and 20 mm.

9. The guide for intramedullary reamer according to claim 1, wherein a curvature radius of the non-rectilinear portion of the central body is comprised between 25 mm and 400 mm.

10. The guide for intramedullary reamer according to claim 1, wherein the central body comprises a handle.

11. The guide for intramedullary reamer according to claim 10, wherein said non-rectilinear portion comprises the outlet opening and said handle comprises the inlet opening, said non-rectilinear portion being in fluid communication with said handle.

12. The guide for intramedullary reamer according to claim 11, wherein the non-rectilinear portion is integrally formed with the handle or connectable thereto by interconnection means, said interconnection means providing a fluid connection between said non-rectilinear portion and said handle.

13. The guide for intramedullary reamer according to claim 10, wherein the non-rectilinear portion is integrally formed with the handle or connectable thereto by interconnection means, said interconnection means providing a fluid connection between said non-rectilinear portion and said handle.

14. The guide for intramedullary reamer according to claim 1, wherein said guide is made, at least partially, of plastic or metal material.

15. The guide for intramedullary reamer according to claim 1, wherein a bushing is provided, in proximity to the outlet opening, adapted to protect moving parts of the reamer.

16. The guide for intramedullary reamer according to claim 15, wherein the bushing is made of anti-friction material.

17. The guide for intramedullary reamer according to claim 1, wherein the inlet opening of the central body and the window are in fluid communication with each other through the axial cavity.

\* \* \* \* \*